US006884435B1

(12) United States Patent
O'Hagan et al.

(10) Patent No.: US 6,884,435 B1
(45) Date of Patent: Apr. 26, 2005

(54) MICROPARTICLES WITH ADSORBENT SURFACES, METHODS OF MAKING SAME, AND USES THEREOF

(75) Inventors: Derek O'Hagan, Berkeley, CA (US); Manmohan Singh, Hercules, CA (US); Gary Ott, Oakland, CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 09/581,772

(22) PCT Filed: Jul. 29, 1999

(86) PCT No.: PCT/US99/17308

§ 371 (c)(1),
(2), (4) Date: Jun. 15, 2000

(87) PCT Pub. No.: WO00/06123

PCT Pub. Date: Feb. 10, 2000

Related U.S. Application Data

(63) Continuation-in-part of application No. 09/285,855, filed on Apr. 2, 1999, which is a continuation-in-part of application No. 09/124,533, filed on Jul. 29, 1998, which is a continuation-in-part of application No. 09/015,652, filed on Jan. 29, 1998.

(60) Provisional application No. 60/036,316, filed on Jan. 30, 1997, and provisional application No. 60/069,749, filed on Dec. 16, 1997.

(51) Int. Cl.[7] .......................... A61K 9/14; A61K 31/70; C12N 15/00; C07H 21/00

(52) U.S. Cl. ...................... 424/489; 424/455; 424/490; 514/44; 435/320.1; 536/23.1

(58) Field of Search ............................. 424/1.21, 1.29, 424/9.1, 450, 455, 486, 489, 490, 491, 497, 499, 204.1, 228.1, 278.1, 280.1, 283.1, 208.1, 901, 426, 487, 285.1, 70.11, 70.19, 488; 514/44, 54, 2; 435/320.1, 101; 536/23.1, 300, 350; 436/71; 427/44; 204/499

(56) References Cited

U.S. PATENT DOCUMENTS

| | | | | |
|---|---|---|---|---|
| 4,413,057 A | * | 11/1983 | Carlo et al. | 424/244.1 |
| 4,534,996 A | * | 8/1985 | Rembaum et al. | 427/498 |
| 5,010,183 A | * | 4/1991 | Macfarlane | 435/262 |
| 5,630,922 A | * | 5/1997 | Eswarakrishnan et al. | 204/499 |
| 5,643,605 A | * | 7/1997 | Cleland et al. | 424/279.1 |
| 5,714,354 A | * | 2/1998 | Arnold et al. | 435/101 |
| 5,783,567 A | | 7/1998 | Hedley et al. | 514/44 |
| 5,830,430 A | * | 11/1998 | Unger et al. | 424/1.21 |
| 5,869,103 A | | 2/1999 | Yeh et al. | 424/501 |
| 5,871,747 A | | 2/1999 | Gengoux-Sedlik et al. | 424/208.1 |
| 5,902,565 A | * | 5/1999 | Cox et al. | 424/1.29 |
| 6,086,901 A | | 7/2000 | O'Hagan et al. | 424/283.1 |

FOREIGN PATENT DOCUMENTS

| | | | | |
|---|---|---|---|---|
| WO | WO 94/15635 | 7/1994 | | A61K/39/385 |
| WO | WO 94/28879 | 12/1994 | | A61K/9/16 |
| WO | WO 95/24929 | * | 9/1995 | |
| WO | WO 96/20698 | * | 7/1996 | |
| WO | WO 97/02810 | 1/1997 | | A61K/9/16 |
| WO | WO 97/24447 | 7/1997 | | C12N/15/63 |
| WO | WO 98/10750 | 3/1998 | | A61K/9/16 |
| WO | WO 98/33487 | 8/1998 | | A61K/9/16 |

OTHER PUBLICATIONS

Bertling et al., Use of Lipsomes, Viral Capsids, and Nanoparticles as DNA Carriers, Biotechnology and Applied Biochemistry, vol. 13, pp. 390–405 (1991).*

Moore et al. Vaccine, 13/18:1741–1749, 1995.*

Haynes et al. AIDS Research and Human Retroviruses, 10, Suppl. 2:S42–S45, 1994.*

A.G.A. Coombes et al., "Single Dose, Polymeric, Microparticle–based Vaccines: The Influence of Formulation Conditions on the Magnitude and Duration of the Immune Response to a Protein Antigen," *Vaccine*, 14(15): 1429–1438 (1996).

Jacqueline D. Duncan et al., "Poly(lactide–co–glycolide) Microencapsulation of Vaccines for Mucosal Immunization," *Mucosal Vaccines* (Academic Press, 1996), pp. 159–173.

John H. Eldridge et al., "Biodegradable and Biocompatible Poly(DL–Lactide–Co–Glycolide) Microspheres as an Adjuvant for Staphylococcal Enterotoxin B Toxoid Which Enhances the Level of Toxin–Neutralizing Antibodies," *Infection and Immunity* 59(9):2978–2986 (1991).

John H. Eldridge et al., "New Advances in Vaccines in Vaccine Delivery Systems," *Seminars in Hematology* 30(4):16–25 (1993).

Deborah A. Higgins et al., "MF59 Adjuvant Enhances the Immunogenicity of Influenza Vaccine in Both Young and Old Mice," *Vaccine* 14(6):478–484 (1996).

Ying Men et al., "Induction of a Cytotoxic T Lymphocyte Response by Immunization with a Malaria Specific CTL Peptide Entrapped in Biodegradable Polymer Microspheres," *Vaccine* 15(12–13):1405–1412 (1997).

(Continued)

*Primary Examiner*—James Housel
*Assistant Examiner*—Zachariah Lucas
(74) *Attorney, Agent, or Firm*—David B. Bonham; Alisa A. Harbin; Robert P. Blackburn

(57) ABSTRACT

The present invention is directed to microparticles, to microparticle compositions containing the same, to methods of forming the same, and to uses for the same, including use for a vaccine, for raising an immune response, for treatment of a disease and for diagnosis of a disease. The microparticles comprise a biodegradable polymer, such as a poly(α-hydroxy acid), a polyhydroxy butyric acid, a polycaprolactone, a polyorthoester, a polyanhydride, or a polycyanoacrylate, and a detergent selected from a cationic detergent and an anionic detergent. The microparticles further comprise an antigen adsorbed on the surface of the microparticle.

53 Claims, No Drawings

OTHER PUBLICATIONS

Ryusuke Nakaoka et al., "Enhanced Antibody Production Through Sustained Antigen Release from Biodegradable Granules," *Journal of Controlled Release* 37:215–224 (1995).

D.T. O'Hagan et al., "Long–Term Antibody Responses in Mice Following Subcutaneous Immunization with Ovalbumin Entrapped in Biodegradable Particles," *Vaccine* 11(9):965–969 (1993).

D.T. O'Hagan et al., "Biodegradable Microparticles for Oral Immunization," *Vaccine* 11:149–154 (1993).

Michael F. Powell et al., eds., *Vaccine Design: The Subunit and Adjuvant Approach*, Plenum Press, New York, p. 183 (1995).

Hongkee Sah et al., "Continuous Release of Proteins from Biodegradable Microcapsules and in Vivo Evaluation of Their Potential as a Vaccine Adjuvant," *Journal of Controlled Release* 35:137–144 (1995).

H.M. Vordermeier et al., "Synthetic Delivery System for Tuberculosis Vaccines: Immunological Evaluation of the *M. tuberculosis* 38 kDa Protein Entrapped in Biodegradable PLG Microparticles," *Vaccine* 13(16):1576–1582 (1995).

Chavany, Christine et al., "Adsorption of Oligonucleotides onto Polyisohexylcyanoacrylate Nanoparticles Protects Them Against Nucleases and Increases Their Cellular Uptake," Pharmaceutical Research, vol. 11, No. 9, 1994, pp. 1370–1378.

Fattal, Elias et al., "Biodegradable polyalkylcyanoacrylate nanoparticles for the delivery of olionucleotides," Journal of Controlled Release 53 (1998), pp. 137–143.

* cited by examiner

MICROPARTICLES WITH ADSORBENT SURFACES, METHODS OF MAKING SAME, AND USES THEREOF

CROSS-REFERENCE TO RELATED APPLICATIONS

This application is a continuation-in-part of U.S. patent application Ser. No. 09/285,855, filed Apr. 2, 1999, from which priority is claimed under 35 U.S.C. 120 and which application is incorporated herein by reference in its entirety, which is a continuation-in-part of U.S. patent application Ser. No. 09/124,533, filed Jul. 29, 1998, from which priority is claimed under 35 U.S.C. 120 and which application is incorporated herein by reference in its entirety, which is a continuation-in-part of U.S. patent application Ser. No. 09/015,652, filed Jan. 29, 1998, from which priority is claimed under 35 U.S.C. 120 and which application is incorporated herein by reference in its entirety, which in turn is related to U.S. provisional patent application Ser. Nos. 60/036,316, filed Jan. 30, 1997 and 60/069,749, filed Dec. 16, 1997, from which applications priority is claimed under 35 U.S.C. 119(e)(1), and which applications are incorporated herein by reference in their entireties.

TECHNICAL FIELD

The present invention relates generally to pharmaceutical compositions. In particular, the invention relates to microparticles with adsorbent surfaces, methods for preparing such microparticles, and uses thereof Additionally, the invention relates to compositions comprising biodegradable microparticles where in biologically active agents, such as therapeutic polynucleotides, polypeptides, antigens, and adjuvants, are adsorbed on the surface of the microparticles.

BACKGROUND

Particulate carriers have been used in order to achieve controlled, parenteral delivery of therapeutic compounds. Such carriers are designed to maintain the active agent in the delivery system for an extended period of time. Examples of particulate carriers include those derived from polymethyl methacrylate polymers, as well as microparticles derived from poly(lactides) (see, e.g., U.S. Pat. No. 3,773,919), poly(lactide-co-glycolides), known as PLG (see, e.g., U.S. Pat. No. 4,767,628) and polyethylene glycol, known as PEG (see, e.g., U.S. Pat. No. 5,648,095). Polymethyl methacrylate polymers are nondegradable while PLG particles biodegrade by random nonenzymatic hydrolysis of ester bonds to lactic and glycolic acids which are excreted along normal metabolic pathways.

For example, U.S. Pat. No. 5,648,095 describes the use of microspheres with encapsulated pharmaceuticals as drug delivery systems for nasal, oral, pulmonary and oral delivery. Slow-release formulations containing various polypeptide growth factors have also been described. See, e.g., International Publication No. WO 94/12158, U.S. Pat. No. 5,134,122 and International Publication No. WO 96/37216.

Fattal et al., Journal of Controlled Release 53:137–143 (1998) describes nanoparticles prepared from polyalkylcyanoacrylates (PACA) having adsorbed oligonucleotides.

Particulate carriers have also been used with adsorbed or entrapped antigens in attempts to elicit adequate immune responses. Such carriers present multiple copies of a selected antigen to the immune system and promote trapping and retention of antigens in local lymph nodes. The particles can be phagocytosed by macrophages and can enhance antigen presentation through cytokine release. For example, commonly owned, co-pending application Ser. No. 09/015,652, filed Jan. 29, 1998, describes the use of antigen-adsorbed and antigen-encapsulated microparticles to stimulate cell-mediated immunological responses, as well as methods of making the microparticles.

In commonly owned provisional Patent Application 60/036,316, for example, a method of forming microparticles is disclosed which comprises combining a polymer with an organic solvent, then adding an emulsion stabilizer, such as polyvinyl alcohol (PVA), then evaporating the organic solvent, thereby forming microparticles. The surface of the microparticles comprises the polymer and the stabilizer, Macromolecules such as DNA, polypeptides, and antigens may then be adsorbed on those surfaces.

It has also been shown that cationic lipid-based emulsions may be used as gene carriers. See, e.g., Yi et al., *Cationic Lipid Emulsion; a Novel Non-Viral*, and *Non-Liposomal Gene Delivery System*, Proc. Int'l. Symp. Control. Rel. Bioact. Mater., 24:653–654 (1997); Kim et al., *In Vivo Gene Transfer Using Cationic Lipid Emulsion-Mediated Gene Delivery System by Intra Nasal Administration*, Proc. Int'l. Symp. Control. Rel. Bioact. Mater., 25:344–345 (1998); Kim et al., *In Vitro and In Vivo Gene Delivery Using Cationic Lipid Emulsion*, Proc. Int'l. Symp. Control. Rel. Bioact. Mater., 26, #5438 (1999).

While antigen-adsorbed PLG microparticles offer significant advantages over other more toxic systems, adsorption of biologically active agents to the microparticle surface can be problematic. For example, it is often difficult or impossible to adsorb charged or bulky biologically active agents, such as polynucleotides, large polypeptides, and the like, to the microparticle surface. Thus, there is a continued need for flexible delivery systems for such agents and, particularly for drugs that are highly sensitive and difficult to formulate.

SUMMARY OF THE INVENTION

The inventors herein have invented a method of forming microparticles with adsorbent surfaces capable of adsorbing a wide variety of macromolecules. The microparticles are comprised of both a polymer and a detergent. The microparticles of the present invention adsorb such macromolecules more efficiently than other microparticles currently available.

The microparticles are derived from a polymer, such as a poly($\alpha$-hydroxy acid), a polyhydroxy butyric acid, a polycaprolactone, a polyorthoester, a polyanhydride, a PACA, a polycyanoacrylate, and the like, and are formed with detergents, such as cationic, anionic, or nonionic detergents, which detergents may be used in combination. Additionally, the inventors have discovered that these microparticles yield improved adsorption of viral antigens, and provide for superior immune responses, as compared to microparticles formed by a process using only PVA. While microparticles made using only PVA may adsorb some macromolecules, the microparticles of the present invention using other detergents alone, in combination, or in combination with PVA, adsorb a wide variety of macromolecules. Accordingly, then, the invention is primarily directed to such microparticles, as well as to processes for producing the same and methods of using the microparticles.

In one embodiment, the invention is directed to a microparticle with an adsorbent surface, wherein the microparticle comprises a polymer selected from the group consisting of a poly($\alpha$-hydroxy acid), a polyhydroxy butyric acid, a polycaprolactone, a polyorthoester, a polyanhydride, and a polycyanoacrylate.

In another embodiment, the invention is directed to such microparticles which further comprise a selected macromolecule adsorbed on the microparticle's surface, such as a pharmaceutical, a polynucleotide, a polypeptide, a protein, a hormone, an enzyme, a transcription or translation mediator, an intermediate in a metabolic pathway, an immunomodulator, an antigen, an adjuvant, or combinations thereof, and the like.

In another embodiment, the invention is directed to a microparticle composition comprising a selected macromolecule adsorbed to a microparticle of the invention and a pharmaceutically acceptable excipient.

In another embodiment, the invention is directed to a microparticle comprising a biodegradable polymer and an ionic surfactant.

In another embodiment, the invention is directed to a method of producing a microparticle having an adsorbent surface, the method comprising:
  (a) combining a polymer solution comprising a polymer selected from the group consisting of a poly(a-hydroxy acid), a polyhydroxy butyric acid, a polycaprolactone, a polyorthoester, a polyanhydride, and a polycyanoacrylate, wherein the polymer is present at a concentration of about 1% to about 30% in an organic solvent;
  and an anionic, cationic, or nonionic detergent to the polymer solution, wherein the detergent is present at a ratio of 0.001 to 10 (w/w) detergent to polymer, to form a polymer/detergent mixture;
  (b) dispersing the polymer/detergent mixture;
  (c) removing the organic solvent; and
  (d) recovering the microparticle.

Preferably, the polymer/detergent mixture is emulsfied to form an emulsion prior to removing the organic solvent.

In another embodiment, the invention is directed to a microparticle produced by the above described methods.

In another embodiment, the invention is directed to a method of producing a microparticle with an adsorbed macromolecule comprising:
  (a) combining a polymer solution comprising poly(D,L-lactide-co-glycolide), wherein the polymer is present at a concentration of about 3% to about 10% in an organic solvent;
  and an anionic, cationic, or nonionic detergent, wherein the detergent is present at a ratio of 0.001 to 10 (w/w) detergent to polymer, to form a polymer/detergent mixture;
  (b) dispersing the polymer/detergent mixture;
  (c) removing the organic solvent from the emulsion;
  (d) recovering the microparticle; and
  (e) adsorbing a macromolecule to the surface of the microparticle, wherein the macromolecule is selected from the group consisting of a pharmaceutical, a polynucleotide, a polypeptide, a hormone, an enzyme, a transcription or translation mediator, an intermediate in a metabolic pathway, an immunomodulator, an antigen, an adjuvant, and combinations thereof Preferably, the polymer/detergent mixture is emulsfied to form an emulsion prior to removing the organic solvent. In another embodiment, the invention is directed to a microparticle with an adsorbed macromolecule produced by the above described method.

In another embodiment, the invention is directed to a method of producing an adsorbent microparticle composition comprising combining an adsorbent microparticle having a macromolecule adsorbed on the surface thereof and a pharmaceutically acceptable excipient.

In yet another embodiment, the invention is directed to a method of delivering a macromolecule to a vertebrate subject which comprises administering to a vertebrate subject the composition above.

In an additional embodiment, the invention is directed to a method for eliciting a cellular immune response in a vertebrate subject comprising administering to a vertebrate subject a therapeutically effective amount of a selected macromolecule adsorbed to a microparticle of the invention.

In another embodiment, the invention is directed to a method of immunization which comprises administering to a vertebrate subject a therapeutically effective amount of the microparticle composition above. The composition may optionally contain unbound macromolecules, and also may optionally contain adjuvants, including aluminum salts such as aluminum phosphate.

In a preferred embodiment, the microparticles are formed from a poly(α-hydroxy acid); more preferably, a poly(D,L-lactide-co-glycolide); and most preferably, a poly(D,L-lactide-co-glycolide).

In a preferred embodiment, the microparticles are for use in diagnosis of a disease.

In a preferred embodiment, the microparticles are for use in treatment of a disease.

In a preferred embodiment, the microparticles are for use in a vaccine.

In a preferred embodiment, the microparticles are for use in raising an immune response.

Each of the nonexhaustive previously described adsorbent microparticles may optionally also have macromolecules entrapped within them.

These and other embodiments of the present invention will readily occur to those of ordinary skill in the art in view of the disclosure herein.

DETAILED DESCRIPTION OF THE INVENTION

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); *Handbook of Experimental Immunology*, Vols. I–IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S., ed, CRC Press, 1997) and *Seymour/Carraher's Polymer Chemistry* (4th edition, Marcel Dekker Inc., 1996).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, the term "a microparticle" refers to one or more microparticles, and the like.

A. Definitions

In describing the present invention, the following terms will be employed, and are intended to be defined as indicated below.

The term "microparticle" as used herein, refers to a particle of about 100 nm to about 150 μm in diameter, more preferably about 200 nm to about 30 μm in diameter, and most preferably about 500 nm to about 10 μm in diameter. Preferably, the microparticle will be of a diameter that permits parenteral or mucosal administration without occluding needles and capillaries. Microparticle size is readily determined by techniques well known in the art, such as photon correlation spectroscopy, laser diffractometry and/or scanning electron microscopy.

Microparticles for use herein will be formed from materials that are sterilizable, non-toxic and biodegradable. Such materials include, without limitation, poly(a-hydroxy acid), polyhydroxybutyric acid, polycaprolactone, polyorthoester, polyanhydride, PACA, and polycyanoacrylate. Preferably, microparticles for use with the present invention are derived from a poly(α-hydroxy acid), in particular, from a poly (lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered macromolecule. These parameters are discussed more fully below.

The term "detergent" as used herein includes surfactants and emulsion stabilizers. Anionic detergents include, but are not limited to, SDS, SLS, sulphated fatty alcohols, and the like. Cationic detergents include, but are not limited to, cetrimide (CTAB), benzalkonium chloride, DDA (dimethyl dioctodecyl ammonium bromide), DOTAP, and the like. Nonionic detergents include, but are not limited to, sorbitan esters, polysorbates, polyoxyethylated glycol monoethers, polyoxyethylated alkyl phenols, poloxamers, and the like.

The term "net positive charge" as used herein, means that the charge on the surface of the microparticle is more positive than the charge on the surface of a corresponding microparticle made using PVA. Likewise, the term "net negative charge" as used herein, means that the charge on the surface of the microparticle is more negative than the charge on the surface of a corresponding microparticle made using PVA. Net charge can be assessed by comparing the zeta potential (also known as electrokinetic potential) of the microparticle made using a cationic or anionic detergent with a corresponding microparticle made using PVA. Thus, a microparticle surface having a "net positive charge" will have a zeta potential greater than the zeta potential of the surface of a microparticle made using PVA and a microparticle having a "net negative charge" will have a zeta potential less than the zeta potential of the surface of a microparticle made using PVA. As is apparent, the net charges for the microparticles of the invention are calculated relative to the zeta potential of a corresponding PVA microparticle.

The term "zeta potential" as used herein, refers to the electrical potential that exists across the interface of all solids and liquids, i.e., the potential across the diffuse layer of ions surrounding a charged colloidal particle. Zeta potential can be calculated from electrophoretic mobilities, i.e., the rates at which colloidal particles travel between charged electrodes placed in contact with the substance to be measured, using techniques well known in the art.

The term "macromolecule," as used herein, refers to, without limitation, a pharmaceutical, a polynucleotide, a polypeptide, a hormone, an enzyme, a transcription or translation mediator, an intermediate in a metabolic pathway, an immunomodulator, an antigen, an adjuvant, or combinations thereof. Particular macromolecules for use with the present invention are described in more detail below.

The term "pharmaceutical" refers to biologically active compounds such as antibiotics, antiviral agents, growth factors, hormones, and the like, discussed in more detail below.

A "polynucleotide" is a nucleic acid molecule which encodes a biologically active (e.g., immunogenic or therapeutic) protein or polypeptide. Depending on the nature of the polypeptide encoded by the polynucleotide, a polynucleotide can include as little as 10 nucleotides, e.g., where the polynucleotide encodes an antigen. Furthermore, a "polynucleotide" can include both double- and single-stranded sequences and refers to, but is not limited to, cDNA from viral, procaryotic or eucaryotic mRNA, genomic RNA and DNA sequences from viral (e.g. RNA and DNA viruses and retroviruses) or procaryotic DNA, and especially synthetic DNA sequences. The term also captures sequences that include any of the known base analogs of DNA and RNA, and includes modifications, such as deletions, additions and substitutions (generally conservative in nature), to the native sequence, so long as the nucleic acid molecule encodes a therapeutic or antigenic protein. These modifications may be deliberate, as through site-directed mutagenesis, or may be accidental, such as through mutations of hosts which produce the antigens.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to the native sequence, so long as the protein maintains the ability to elicit an immunological response or have a therapeutic effect on a subject to which the protein is administered.

By "antigen" is meant a molecule which contains one or more epitopes capable of stimulating a host's immune system to make a cellular antigen-specific immune response when the antigen is presented in accordance with the present invention, or a humoral antibody response. An antigen may be capable of eliciting a cellular or humoral response by itself or when present in combination with another molecule. Normally, an epitope will include between about 3–15, generally about 5–15, amino acids. Epitopes of a given protein can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1986) *Molec. Immunol.* 23:709–715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra.

The term "antigen" as used herein denotes both subunit antigens, i.e., antigens which are separate and discrete from a whole organism with which the antigen is associated in nature, as well as killed, attenuated or inactivated bacteria, viruses, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses a therapeutic or immunogenic protein, or antigenic determinant in vivo, such as in gene therapy and nucleic acid immunization applications, is also included in the definition of antigen herein.

Further, for purposes of the present invention, antigens can be derived from any of several known viruses, bacteria, parasites and fungi, as well as any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

An "immunological response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL's"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition, such as an immunogenic composition, or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189–4199; Doe et al., *Eur. J Immunol.* (1994) 24:2369–2376; and the examples below.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

A composition which contains a selected antigen adsorbed to a microparticle, displays "enhanced immunogenicity" when it possesses a greater capacity to elicit an immune response than the immune response elicited by an equivalent amount of the antigen when delivered without association with the microparticle. Thus, a composition may display "enhanced immunogenicity" because the antigen is more strongly immunogenic by virtue of adsorption to the microparticle, or because a lower dose of antigen is necessary to achieve an immune response in the subject to which it is, administered. Such enhanced immunogenicity can be determined by administering the microparticle/antigen composition, and antigen controls to animals and comparing antibody titers against the two using standard assays such as radioimmunoassay and ELISAs, well known in the art.

The terms "effective amount" or "pharmaceutically effective amount" of a macromolecule/microparticle, as provided herein, refer to a nontoxic but sufficient amount of the macromolecule/microparticle to provide the desired response, such as an immunological response, and corresponding therapeutic effect, or in the case of delivery of a therapeutic protein, an amount sufficient to effect treatment of the subject, as defined below. As will be pointed out below, the exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

By "vertebrate subject" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are intended to be covered.

By "pharmaceutically acceptable" or "pharmacologically acceptable" is meant a material which is not biologically or otherwise undesirable, i.e., the material may be administered to an individual along with the microparticle formulation without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, "treatment" refers to any of (i) the prevention of infection or reinfection, as in a traditional vaccine, (ii) the reduction or elimination of symptoms, and (iii) the substantial or complete elimination of the pathogen or disorder in question. Treatment may be effected prophylactically (prior to infection) or therapeutically (following infection).

B. General Methods

The present invention is based on the discovery that the PLA and PLG microparticles of the present invention efficiently adsorb biologically active macromolecules. Further, these microparticles adsorb a greater variety of molecules, including charged and/or bulky macromolecules, more readily than microparticles prepared with PVA. Thus the macromolecule/microparticle of the present invention can be used as a delivery system to deliver the biologically active components in order to treat, prevent and/or diagnose a wide variety of diseases.

The present invention can be used to deliver a wide variety of macromolecules including, but not limited to, pharmaceuticals such as antibiotics and antiviral agents, nonsteroidal antiinflammatory drugs, analgesics, vasodilators, cardiovascular drugs, psychotropics, neuroleptics, antidepressants, antiparkinson drugs, beta blockers, calcium channel blockers, bradykinin inhibitors, ACE-inhibitors, vasodilators, prolactin inhibitors, steroids, hormone antagonists, antihistamines, serotonin antagonists, heparin, chemotherapeutic agents, antineoplastics and growth factors, including but not limited to PDGF, EGF, KGF, IGF-1 and IGF-2, FGF, polynucleotides which encode therapeutic or immunogenic proteins, immunogenic proteins and epitopes thereof for use in vaccines, hormones including peptide hormones such as insulin, proinsulin, growth hormone, GHRH, LHRH, EGF, somatostatin, SNX-111, BNP, insulinotropin, ANP, FSH, LH, PSH and hCG, gonadal steroid hormones (androgens, estrogens and progesterone), thyroid-stimulating hormone, inhibin, cholecystokinin, ACTH, CRF, dynorphins, endorphins, endothelin, fibronectin fragments, galanin, gastrin, insulinotropin, glucagon, GTP-binding protein fragments, guanylin, the leukokiniris, magainin, mastoparans, dermaseptin, systemin, neuromedins, neurotensin, pancreastatin, pancreatic polypeptide, substance P, secretin, thymosin, and the like, enzymes, transcription or translation mediators, intermediates in metabolic pathways, immunomodulators, such as any of the various cytokines including interleukin-1, interleukin-2, interleukin-3, interleukin-4, and gamma-interferon, antigens, and adjuvants.

In a preferred embodiment the macromolecule is an antigen. A particular advantage of the present invention is the ability of the microparticles with adsorbed antigen to generate cell-mediated immune responses in a vertebrate subject. The ability of the antigen/microparticles of the present invention to elicit a cell-mediated immune response against a selected antigen provides a powerful tool against infection by a wide variety of pathogens. Accordingly, the antigen/microparticles of the present invention can be incorporated into vaccine compositions.

Thus, in addition to a conventional antibody response, the system herein described can provide for, e.g., the association of the expressed antigens with class I MHC molecules such that an in vivo cellular immune response to the antigen of interest can be mounted which stimulates the production of CTLs to allow for future recognition of the antigen. Furthermore, the methods may elicit an antigen-specific response by helper T-cells. Accordingly, the methods of the present invention will find use with any macromolecule for which cellular and/or humoral immune responses are desired, preferably antigens derived from viral pathogens that may induce antibodies, T-cell helper epitopes and T-cell cytotoxic epitopes. Such antigens include, but are not limited to, those encoded by human and animal viruses and can correspond to either structural or non-structural proteins.

The microparticles of the present invention are particularly useful for immunization against intracellular viruses which normally elicit poor immune responses. For example, the present invention will find use for stimulating an immune response against a wide variety of proteins from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., *Cytomegaloviruses* (J. K. McDougall, ed., Springer-Verlag 1990) pp. 125–169, for a review of the protein coding content of cytomegalovirus; McGeoch et al., *J Gen. Virol.* (1988) 69:1531–1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207–211, for the identification of protein coding sequences in an EBV genome; and Davison and Scott, *J. Gen. Virol.* (1986) 67:1759–1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NS1) and an N-terminal nucleocapsid protein (termed "core") (see, Houghton et al., Hepatology (1991) 14:381–388, for a discussion of HCV proteins, including E1 and E2). Each of these proteins, as well as antigenic fragments thereof, will find use in the present composition and methods.

Similarly, the sequence for the δ-antigen from HDV is known (see, e.g., U.S. Pat. No. 5,378,814) and this antigen can also be conveniently used in the present composition and methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., "HBV Vaccines—from the laboratory to license: a case study" in Mackett, M. and Williamson, J. D., *Human Vaccines and Vaccination*, pp. 159–176, for a discussion of HBV structure; and U.S. Pat. Nos. 4,722,840, 5,098,704, 5,324,513, incorporated herein by reference in their entireties; Beames et al., *J Virol.* (1995) 69:6833–6838, Birnbaum et al., *J. Virol.* (1990) 64:3319–3330; and Zhou et al., *J. Virol.* (1991) 65:5457–5464.

Antigens derived from other viruses will also find use in the claimed compositions and methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LA1, HIVMN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); *Fundamental Virology*, 2nd Edition (B. N. Fields and D. M. Knipe, eds. 1991), for a description of these and other viruses.

More particularly, the gp120 envelope proteins from any of the above HIV isolates, including members of the various genetic subtypes of HIV, are known and reported (see, e.g., Myers et al., Los Alamos Database, Los Alamos National Laboratory, Los Alamos, N.Mex. (1992); Myers et al., *Human Retroviruses and Aids*, 1990, Los Alamos, N.Mex.: Los Alamos National Laboratory; and Modrow et al., *J Virol.* (1987) 61:570–578, for a comparison of the envelope sequences of a variety of HIV isolates) and antigens derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol region.

Influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759–767; Webster et al., "Antigenic variation among type A influenza viruses," p. 127–168. In: P. Palese and D. W. Kingsbury (ed.), *Genetics of influenza viruses*. Springer-Verlag, New York). Thus, proteins derived from any of these isolates can also be used in the compositions and methods described herein.

The compositions and methods described herein will also find use with numerous bacterial antigens, such as those derived from organisms that cause diphtheria, cholera, tuberculosis, tetanus, pertussis, meningitis, and other pathogenic states, including, without limitation, *Bordetella pertussis*, *Neisseria meningitides* (A, B, C, Y), *Neisseria gonorrhoeae, Helicobacter pylori*, and *Haemophilus influenza. Hemophilus influenza* type B (HIB), *Helicobacter pylori*, and combinations thereof. Examples of antigens from *Neisseria meningitides* B are disclosed in the following co-owned patent applications: PCT/US99/09346; PCT IB98/01665; PCT IB99/00103; and U.S. Provisional Applications Serial Nos. 60/083,758; 60/094,869; 60/098,994; 60/103,749; 60/103,794; 60/103,796; and 60/121,528. Examples of parasitic antigens include those derived from organisms causing malaria and Lyme disease.

It is readily apparent that the subject invention can be used to deliver a wide variety of macromolecules and hence to treat, prevent and/or diagnose a large number of diseases. In an alternative embodiment, the macromolecule/microparticle compositions of the present invention can be used for site-specific targeted delivery. For example, intravenous administration of the macromolecule/microparticle compositions can be used for targeting the lung, liver, spleen, blood circulation, or bone marrow.

The adsorption of macromolecules to the surface of the adsorbent microparticles occurs via any bonding-interaction mechanism, including, but not limited to, ionic bonding, hydrogen bonding, covalent bonding, Van der Waals bonding, and bonding through hydrophilic/hydrophobic interactions. Those of ordinary skill in the art may readily select detergents appropriate for the type of macromolecule to be adsorbed.

For example, microparticles manufactured in the presence of charged detergents, such as anionic or cationic detergents, may yield microparticles with a surface having a net negative or a net positive charge, which can adsorb a wide variety of molecules. For example, microparticles manufactured with anionic detergents, such as sodium dodecyl sulfate (SDS), i.e. SDS-PLG microparticles, adsorb positively charged antigens, such as proteins. Similarly, microparticles manufactured with cationic detergents, such as hexadecyltrimethylammonium bromide (CTAB), i.e. CTAB-PLG microparticles, adsorb negatively charged macromolecules, such as DNA. Where the macromolecules to be adsorbed have regions of positive and negative charge, either cationic or anionic detergents may be appropriate.

Biodegradable polymers for manufacturing microparticles for use with the present invention are readily commercially available from, e.g., Boehringer Ingelheim, Germany and Birmingham Polymers, Inc., Birmingham, Ala. For example, useful polymers for forming the microparticles herein include those derived from polyhydroxybutyric acid; polycaprolactone; polyorthoester; polyanhydride; as well as a poly(α-hydroxy acid), such as poly(L-lactide), poly(D,L-lactide) (both known as "PLA" herein), poly (hydoxybutyrate), copolymers of D,L-lactide and glycolide, such as poly(D,L-lactide-co-glycolide) (designated as "PLG" or "PLGA" herein) or a copolymer of D,L-lactide and caprolactone. Particularly preferred polymers for use herein are PLA and PLG polymers. These polymers are available in a variety of molecular weights, and the appropriate molecular weight for a given use is readily determined by one of skill in the art. Thus, e.g., for PLA, a suitable molecular weight will be on the order of about 2000 to 5000. For PLG, suitable molecular weights will generally range from about 10,000 to about 200,000, preferably about 15,000 to about 150,000, and most preferably about 50,000 to about 100,000.

If a copolymer such as PLG is used to form the microparticles, a variety of lactide:glycolide ratios will find use herein and the ratio is largely a matter of choice, depending in part on the coadministered macromolecule and the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. It is readily apparent that a suitable ratio of lactide:glycolide is easily determined by one of skill in the art based on the nature of the antigen and disorder in question. Moreover, mixtures of microparticles with varying lactide:glycolide ratios will find use herein in order to achieve the desired release kinetics for a given macromolecule and to provide for both a primary and secondary immune response. Degradation rate of the microparticles of the present invention can also be controlled by such factors as polymer molecular weight and polymer crystallinity. PLG copolymers with varying lactide::glycolide ratios and molecular weights are readily available commercially from a number of sources including from Boehringer Ingelheim, Germany and Birmingham Polymers, Inc., Birmingham, Ala. These polymers can also be synthesized by simple polycondensation of the lactic acid component using techniques well known in the art, such as described in Tabata et al., *J. Biomed. Mater. Res.* (1988) 22:837–858.

The macromolecule/microparticles are prepared using any of several methods well known in the art. For example, double emulsion/solvent evaporation techniques, such as those described in U.S. Pat. No. 3,523,907 and Ogawa et al., *Chem. Pharm. Bull.* (1988) 36:1095–1103, can be used herein to make the microparticles. These techniques involve the formation of a primary emulsion consisting of droplets of polymer solution, which is subsequently mixed with a continuous aqueous phase containing a particle stabilizer/surfactant.

Alternatively, a water-in-oil-in-water (w/o/w) solvent evaporation system can be used to form the microparticles, as described by O'Hagan et al., *Vaccine* (1993) 11:965–969 and Jeffery et al., Pharm. Res. (1993) 10:362. In this technique, the particular polymer is combined with an organic solvent, such as ethyl acetate, dimethylchloride (also called methylene chloride and dichloromethane), acetonitrile, acetone, chloroform, and the like. The polymer will be provided in about a 1–30%, preferably about a 2–15%, more preferably about a 3–10% and most preferably, about a 4% solution, in organic solvent. The polymer solution is emulsified using e.g., an homogenizer. The emulsion is then optionally combined with a larger volume of an aqueous solution of an emulsion stabilizer such as polyvinyl alcohol (PVA), polyvinyl pyrrolidone, and a cationic, anionic, or nonionic detergent. The emulsion may be combined with more than one emulsion stabilizer and/or detergent, e.g., a combination of PVA and a detergent. Certain macromolecules may adsorb more readily to microparticles having a combination of stabilizers and/or detergents. Where an emulsion stabilizer is used, it is typically provided in about a 2–15% solution, more typically about a 4–10% solution. Generally, a weight to weight detergent to polymer ratio in the range of from about 0.00001:1 to about 0.1:1 will be used, more preferably from about 0.0001:1 to about 0.01:1, more preferably from about 0.001:1 to about 0.01:1, and even more preferably from about 0.005:1 to about 0.01:1. The mixture is then homogenized to produce a stable w/o/w double emulsion. Organic solvents are then evaporated.

The formulation parameters can be manipulated to allow the preparation of small microparticles on the order of 0.05 µm (50 nm) to larger microparticles 50 µm or even larger. See, e.g., Jeffery et al., *Pharm. Res.* (1993) 10:362–368; McGee et al., *J. Microencap.* (1996). For example, reduced agitation results in larger microparticles, as does an increase in internal phase volume. Small particles are produced by low aqueous phase volumes with high concentrations of emulsion stabilizers.

Microparticles can also be formed using spray-drying and coacervation as described in, e.g., Thomasin et al., *J. Controlled Release* (1996) 41:131; U.S. Pat. No. 2,800,457; Masters, sit K. (1976) *Spray Drying* 2nd Ed. Wiley, N.Y.; air-suspension coating techniques, such as pan coating and Wurster coating, as described by Hall et al., (1980) The "Wurster Process" in *Controlled Release Technologies: Methods, Theory, and Applications* (A. F. Kydonieus, ed.), Vol. 2, pp. 133–154 CRC Press, Boca Raton, Fla. and Deasy, P. B., *Crit. Rev. Ther. Drug Carrier Syst.* (1988) S(2):99–139; and ionic gelation as described by, e.g., Lim et al., *Science* (1980) 210:908–910.

Particle size can be determined by, e.g., laser light scattering, using for example, a spectrometer incorporating a helium-neon laser. Generally, particle size is determined at room temperature and involves multiple analyses of the sample in question (e.g., 5–10 times) to yield an average value for the particle diameter. Particle size is also readily determined using scanning electron microscopy (SEM).

Following preparation, microparticles can be stored as is or freeze-dried for future use. In order to adsorb macromolecules to the microparticles, the microparticle preparation is simply mixed with the macromolecule of interest and the resulting formulation can again be lyophilized prior to use. Generally, macromolecules are added to the microparticles to yield microparticles with adsorbed macromolecules having a weight to weight ratio of from about 0.0001:1 to 0.25:1 macromolecules to microparticles, preferably, 0.001:1 to 0.1, more preferably 0.01 to 0.05. Macromolecule content of the microparticles can be determined using standard techniques.

The microparticles of the present invention may have macromolecules entrapped or encapsulated within them, as well as having macromolecules adsorbed thereon. Thus, for example, one of skill in the art may prepare in accordance with the invention microparticles having encapsulated adjuvants with proteins adsorbed thereon, or microparticles having encapsulated proteins with adjuvants adsorbed thereon.

Once the macromolecule adsorbed microparticles are produced, they are formulated into pharmaceutical compositions or vaccines, to treat, prevent and/or diagnose a wide variety of disorders, as described above. The compositions will generally include one or more "pharmaceutically acceptable excipients or vehicles" such as water, saline, glycerol, polyethylene-glycol, hyaluronic acid, ethanol, etc. Additionally, auxiliary substances, such as wetting or emulsifying agents, biological buffering substances, and the like, may be present in such vehicles. A biological buffer can be virtually any solution which is pharmacologically acceptable and which provides the formulation with the desired pH, i.e., a pH in the physiological range. Examples of buffer solutions include saline, phosphate buffered saline, Tris buffered saline, Hank's buffered saline, and the like.

Adjuvants may be used to enhance the effectiveness of the pharmaceutical compositions. The adjuvants may be administered concurrently with the microparticles of the present invention, e.g., in the same composition or in separate compositions. Alternatively, an adjuvant may be administered prior or subsequent to the microparticle compositions of the present invention. In another embodiment, the adjuvant, such as an immunological adjuvant, may be encapsulated in the microparticle. Adjuvants, just as any macromolecules, may be encapsulated within the microparticles using any of the several methods known in the art. See, e.g., U.S. Pat. No. 3,523,907; Ogawa et al., *Chem Pharm. Bull.* (1988) 36:1095–1103; O'Hagan et al., *Vaccine* (1993) 11:965–969 and Jefferey et al., *Pharm. Res.* (1993) 10:362. Alternatively, adjuvants may be adsorbed on the microparticle as described above for any macromolecule.

Immunological adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c)

Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™) (for a further discussion of suitable submicron oil-in-water emulsions for use herein, see commonly owned, patent application Ser. No. 09/015,736, filed on Jan. 29, 1998); (3) saponin adjuvants, such as QS21 (e.g., Stimulon™ (Cambridge Bioscience, Worcester, Mass.)) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); (7) CpG oligonucleotides and other immunostimulating sequences (ISSs); and (8) other substances that act as immunostimulating agents to enhance the effectiveness of the composition. Alum and MF59 are preferred.

Muramyl peptides include, but are not limited to, N-acetyl-muramyl-L-threonyl-D-isoglutamnine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylanine (MTP-PE), etc.

For additional examples of adjuvants, see *Vaccine Design, The Subunit and the Adjuvant Approach*, Powell, M. F. and Newman, M. J, eds., Plenum Press, 1995)

The compositions will comprise a "therapeutically effective amount" of the macromolecule of interest. That is, an amount of macromolecule/microparticle will be included in the compositions which will cause the subject to produce a sufficient response, in order to prevent, reduce, eliminate or diagnose symptoms. The exact amount necessary will vary, depending on the subject being treated; the age and general condition of the subject to be treated; the severity of the condition being treated; in the case of an immunological response, the capacity of the subject's immune system to synthesize antibodies; the degree of protection desired and the particular antigen selected and its mode of administration, among other factors. An appropriate effective amount can be readily determined by one of skill in the art. Thus, a "therapeutically effective amount" will fall in a relatively broad range that can be determined through routine trials. For example, for purposes of the present invention, where the macromolecule is a polynucleotide, an effective dose will typically range from about 1 ng to about 1 mg, more preferably from about 10 ng to about 1 μg, and most preferably about 50 ng to about 500 ng of the macromolecule delivered per dose; where the macromolecule is an antigen, an effective dose will typically range from about 1 μg to about 100 mg, more preferably from about 10 μg to about 1 mg, and most preferably about 50 μg to about 500 μg of the macromolecule delivered per dose.

Once formulated, the compositions of the invention can be administered parenterally, e.g., by injection. The compositions can be injected either subcutaneously, intraperitoneally, intravenously or intramuscularly. Other modes of administration include nasal, oral and pulmonary administration, suppositories, and transdermnal or transcutaneous applications. Dosage treatment may be a single dose schedule or a multiple dose schedule. A multiple dose schedule is one in which a primary course of administration may be with 1–10 separate doses, followed by other doses given at subsequent time intervals, chosen to maintain and/or reinforce the therapeutic response, for example at 1–4 months for a second dose, and if needed, a subsequent dose(s) after several months. The dosage regimen will also, at least in part, be determined by the need of the subject and be dependent on the judgment of the practitioner.

Furthermore, if prevention of disease is desired, the macromolecules in vaccines, are generally administered prior to primary infection with the pathogen of interest. If treatment is desired, e.g., the reduction of symptoms or recurrences, the macromolecules are generally administered subsequent to primary infection.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Preparation of Blank Microparticles Using PVA as an Emulsion Stabilizer

Blank microparticles (e.g., without adsorbed or entrapped macromolecules) were made using polyvinyl alcohol (PVA) as follows. Solutions used:

(1) 6% RG 504 PLG (Boehringer Ingelheim) in dichloromethane.

(2) 10% polyvinyl alcohol (PVA) (ICN) in water.

In particular, the microparticles were made by combining 10 ml of polymer solution with 1.0 ml of distilled water and homogenizing for 3 minutes using an Omni benchtop homogenizer with a 10 mm probe at 10K rpm to form a water/oil (w/o) emulsion. The w/o emulsion was added to 40 ml of the 10% PVA solution, and homogenized for 3 minutes, to form a water/oil/water (w/o/w) emulsion. The w/o/w emulsion was left stirring overnight for solvent evaporation, forming microparticles. The formed microparticles were washed with water by centrifugation 4 times, and lyophilized. The microparticles were then sized in a Malvern Master sizer for future use.

EXAMPLE 2

Preparation of Blank Microparticles Using CTAB

Blank microparticles were produced using CTAB as follows. Solutions used:

(1) 4% RG 504 PLG (Boehringer Ingelheim) in dimethyl chloride.

(2) 0.5% CTAB (Sigma Chemical Co., St. Louis, Mo.) in water.

In particular, the microparticles were made by combining 12.5 ml of polymer solution with 1.25 ml of distilled water and homogenizing for 3 minutes using an Omni benchtop homogenizer with a 10 mm probe at 10K rpm to form a w/o emulsion. The w/o emulsion was added to 50 ml of the 0.5% CTAB solution and homogenized for 3 minutes to form a w/o/w emulsion. The w/o/w emulsion was left stirring overnight for solvent evaporation, forming microparticles. The formed microparticles were then filtered through a 38 µ mesh, washed with water by centrifugation 4 times, and lyophilized. The microparticles were then sized in a Malvern Master sizer for future use.

EXAMPLE 3

Preparation of Blank Microparticles Using SDS

Blank microparticles were produced using SDS as follows. Solutions used:

(1) 6% RG 504 PLG (Boehringer Ingelheim) in dimethyl chloride.

(2) % SDS (Sigma Chemical Co., St. Louis, MO) in water.

In particular, the microparticles were made by combining 12.5 ml of polymer solution with 50 ml of the SDS solution and homogenizing for 3 minutes using an Omni benchtop homogenizer with a 10 mm probe at 10K rpm. The emulsion was left stirring overnight for solvent evaporation. The formed microparticles were filtered through a 38 µ mesh, washed with water by centrifugation 4 times, and lyophilized for future use. The microparticles were then sized in a Malvern Master sizer for future use.

EXAMPLE 4

Adsorption of Protein to Blank Microparticles

Protein was adsorbed to microparticles as follows.

A. 1% and 3% Theoretical Load of p55gag

In order to achieve 1% and 3% theoretical loads, 50 mg of the lyophilized blank SDS/PLG microparticles produced as in Example 3 were placed in a Nalgene centrifuge tube and 10 ml of 25 mM Borate buffer, pH 9, with 6M urea containing p55gag protein (Chiron Corporation, Berkeley, Calif.) was added: (a) for 1% theoretical load 10 ml of a 50 µg/ml p55gag solution was used; and (b) for 3% theoretical load 10 ml of a 150µg/ml p55gag solution was used. The mixture was incubated with rocking overnight at room temperature. The next day, the microparticles were centrifuged and the supernatant assayed by a bicinchoninic assay (BCA; Pierce, Rockford, Ill.), for gag concentration to determine the amount adsorbed. The microparticles were washed twice with 10 ml Borate/6M urea buffer and twice with 30 ml water, and lyophilized for future use.

B. 1% Theoretical Load of HCV Core Antigen

In order to achieve 1% theoretical load, 50 mg of the lyophilized blank SDS/PLG microparticles were placed in a Nalgene centrifuge tube and 10 ml of 30 mM citrate buffer, pH 6.5, with 6M urea containing monomeric HCV core protein (10 ml of a 50 µg/ml HCV core protein solution; Chiron Corporation, Berkeley, Calif.) was added. The mixture was incubated with rocking overnight at room temperature. The next day, the microparticles were centrifuged and the supernatant assayed by a bicinchoninic assay (BCA; Pierce, Rockford, Ill.), for HCV concentration to determine the amount adsorbed. The microparticles were washed twice with 30 ml citrate/6M urea buffer and twice with 30 ml water, and lyophilized for future use.

EXAMPLE 5

Adsorption Efficiency of Microparticles

The lyophilized microparticles with adsorbed protein from Example 4 were analyzed for total adsorbed protein using base hydrolysis as follows. 10 mg of the lyophilized adsorbed particles were hydrolyzed for four hours in 2 ml 0.2N NaOH with 5% SDS, neutralized, and diluted 1:10 and analyzed for protein content using the MicroBCA protein assay (Pierce, Rockford, Ill.). As shown in Table 1, microparticles with modified surfaces prepared with detergents like CTAB and SDS, both adsorbed protein more efficiently than microparticles made using solely PVA.

TABLE 1

| Microparticle Type | Protein | Targeted Load (% w/w) | Actual Load (% w/w) |
| --- | --- | --- | --- |
| PVA-PLG | p55gag | 3% | 0.38% |
| CTAB-PLG | p55gag | 3% | 1.58% |
| SDS-PLG | p55gag | 3% | 1.36% |
| PVA-PLG | p55gag | 1% | 0.18% |
| SDS-PLG | p55gag | 0.5% | 0.45% |
| SDS-PLG | p55gag | 1% | 0.72% |
| SDS-PLG | p55gag | 1% | 0.79% |
| PVA-PLG | HCV Core | 4% | 0.3% |
| SDS-PLG | HCV Core | 1% | 0.7% |

EXAMPLE 6

A. Immunogenicity of Gag-adsorbed Microparticles

The gag-adsorbed microparticles, produced using PVA or SDS, as described in Example 4, as well as p55gag alone, without associated microparticles (as a negative control) and vaccinia gag-pol controls (as a positive control) were administered intramuscularly to mice. The animals were boosted at 7 and 14 days. The total dose administered is indicated in Tables 2 and 3. Spleens were collected two weeks following the last immunization and CTL activity assayed as described in Doe et al., *Proc. Natl. Acad. Sci.* (1996) 93:8578–8583.

The lymphocyte cultures were prepared as follows. Spleen cells (sc) from immunized mice were cultured in 24-well dishes at $5 \times 10^6$ cells per well. Of those cells, $1 \times 10^6$ were sensitized with synthetic epitopic peptides form HIV-$1_{SP2}$ proteins at a concentration of 10 µM for 1 hour at 37° C., washed, and cocultured with the remaining $4 \times 10^6$ untreated sc in 2 ml of culture medium [50% RPMI 1640 and 50% alpha-MEM (GIBCO)] supplemented with heat-inactivated fetal calf serum, $5 \times 10^{-5}$ M 2-mercaptoethanol, antibiotics, and 5% interleukin 2 (Rat T-Stim, Collaborative Biomedical Products, Bedford, Mass.). Cells were fed with 1 ml of fresh culture medium on days 3 and 5, and cytotoxicity was assayed on day 6.

The cytotoxic cell assay was conducted as follows. SvBALB ($H-2^d$) (SvB) and MC57 ($H-2^b$) target cells used in the $^{51}$Cr release assays express class I but not class II MHC molecules. Approximately $1 \times 10^6$ target cells were incubated in 200 µl of medium containing 50 µCi (1 Ci=37 Gbq) of $^{51}$Cr and synthetic HIV-1 peptides (1 mM)for 60 min and washed three times. Effector (E) cells were cultured with $5 \times 10^3$ target (T) cells at various E/T ratios in 200 µl of culture medium in 96-well round-bottom tissue culture plates for 4 hours. The average cpm from duplicate wells was used to calculate percent specific $^{51}$Cr release.

As shown in Tables 2 and 3, the SDS-PLG/p55 microparticles had activity comparable to the vaccinia control and was more active than the PVA-PLG/p55 microparticles and the p55gag protein formulation. Specifically, as shown in Table 2, p55gag protein were inactive at concentrations of 10 µg, 25 µg and 50 µg. Further, as shown in Table 3, the SDS-PLG/p55 formulations were more active than the PVA-PLG/p55 and p55gag protein formulations, indicating that proteins were adsorbed more efficiently to the microparticles in the SDS-PLG/p55 formulations as compared to the PVA-PLG/p55 and p55gag protein formulations,

TABLE 2

PERCENT SPECIFIC LYSIS OF TARGETS

| Antigen Adjuvant (Adj. Dose) | Target Ratio | SvB[a] | SvB P7g+[b] | MC57 p7G-[c] |
|---|---|---|---|---|
| p55gag protein (10 μg) | 60 | 15 | 12 | 4 |
| | 15 | 11 | 8 | 3 |
| | 4 | 7 | 6 | 3 |
| % Spon Release | | 12 | 10 | 13 |
| p55gag protein (25 μg) | 63 | 10 | 18 | 2 |
| | 16 | 7 | 6 | −1 |
| | 4 | 4 | 1 | −3 |
| % Spon Release | | 12 | 10 | 13 |
| p55gag protein (50 μg) | 60 | 28 | 22 | 5 |
| | 15 | 13 | 12 | 2 |
| | 4 | 9 | 3 | 3 |
| % Spon Release | | 12 | 10 | 13 |
| p55gag protein (10 μg) PLG/SDS 0.6% 11.6 mg | 60 | 8 | 50 | 0 |
| | 15 | 5 | 21 | −3 |
| | 4 | 4 | 7 | −1 |
| % Spon Release | | 12 | 10 | 13 |
| Vv gag/pol (vaccinia virus encoding gag) | 60 | 9 | 65 | 1 |
| | 15 | 4 | 38 | 1 |
| | 4 | 1 | 18 | 3 |
| % Spon Release | 12 | 10 | 10 | 13 |

[a]SvB cell line without peptide pulsing
[b]SvB cell line pulsed with p7g peptide
[c]MC57 cell line pulsed with p7g peptide

TABLE 3

PERCENT SPECIFIC LYSIS OF TARGETS

| Effector | E:T Ratio | MC57[a] | MC57 + gag b[b] | SVB + gag b[c] |
|---|---|---|---|---|
| PVA-PLG/p55 10 μg | 60:1 | 8 | 15 | 11 |
| | 12:1 | 3 | 10 | 2 |
| | 2.4:1 | >1 | 5 | 2 |
| SDS-PLG/p55 10 μg | 60:1 | 6 | 35 | 4 |
| | 12:1 | 3 | 12 | >1 |
| | 2.4:1 | >1 | 3 | 2 |
| p55gag protein 10 μg | 60:1 | 7 | 15 | 1 |
| | 12:1 | 2 | 6 | 1 |
| | 2.4:1 | >1 | 1 | >1 |
| Vaccinia gag | 60:1 | >1 | 37 | >1 |
| | 12:1 | >1 | 19 | >1 |
| | 2.4:1 | 1 | 9 | >1 |

[a]MC57 cell line without pulsing with peptide
[b]MC57 cell line pulsed with gag b peptide
[c]SVB cell line pulsed with gag b peptide

EXAMPLE 7

Preparation of pCMVgp120 DNA-Adsorbed Microparticles with Modified Surfaces

Microparticles with adsorbed plasmid DNA encoding gp120 were prepared as follows. 20 mg of blank microparticles, prepared as described in Examples 1 and 2, were incubated with increasing concentrations of pCM-Vgp120 DNA in a 1.0 ml volume for 3 hours at 4° C. Following incubation, the microparticles were centrifuged, washed twice with Tris-EDTA buffer and freeze-dried overnight. The microparticles were hydrolyzed as described in Example 5 and analyzed for the amount of adsorbed DNA at $A_{260}$ nm.

Table 4 illustrates the loading efficiency of PLG-PVA and PLG-CTAB microparticles. As indicated in the table, the PLG-CTAB microparticles adsorb more efficiently than the corresponding PLG-PVA particles.

TABLE 4

| Microparticle Type | Theoretical Load (% w/w) | Actual Load (% w/w) | Loading Efficiency (% w/w) |
|---|---|---|---|
| PLG-PVA | 1 | 0.44 | 44 |
| PLG-CTAB | 1 | 0.84 | 88 |
| PLG-PVA | 2 | 0.38 | 19 |
| PLG-CTAB | 2 | 1.23 | 62 |
| PLG-PVA | 3 | 0.33 | 11 |
| PLG-CTAB | 3 | 1.82 | 61 |
| PLG-PVA | 4 | 0.48 | 12 |
| PLG-CTAB | 4 | 2.36 | 59 |

EXAMPLE 8

HCV-E2 Adsorption

Microparticles were prepared using PVA, and several different detergents, as described in the previous examples. E2 protein from Hepatitus C Virus (HCV) was adsorbed on the surface of the microparticles as follows: 0.2 mg/ml E2 was added to 20 mg of the microparticles in PBS to form a solution at 0.5% w/w E2/PLG in a total volume of 0.5 ml. The solutions were incubated for 1.5 hours at 37° C., then centrifuged. The supernatants were collected and then measured for protein content by microBCA. The results are shown in Table 5. The results confirm the superior adsorption of macromolecules by the microparticles of the present invention.

TABLE 5

| Microparticle Type | Protein | % bound (w/w E2/PLG) | % total E2 bound |
|---|---|---|---|
| PVA-PLG | E2 | 0.00 | 0.00 |
| CTAB-PLG | E2 | 0.43 | 96.00 |
| SDS-PLG | E2 | 0.14 | 31.00 |
| NaOleate-PLG | E2 | 0.36 | 81.00 |
| Pluronic P84-PLG | E2 | 0.00 | 0.00 |
| Pluronic L121-PLG | E2 | 0.00 | 0.00 |

EXAMPLE 9

Adsorption of gp120 Protein

Microparticles were prepared using PVA as described in the previous examples.

Microparticles were also prepared using NaOleate, an anionic detergent, as follows: a w/o/w emulsion was prepared with 1.67 ml of 30 mM NaCitrate at pH6 as the internal water phase, 16.7 ml of 6% polymer RG 505 PLG (Boehringer Ingelheim) in dichloromethane as the solvent (oil phase), and 66.8 ml of 0.4% NaOleate as the external aqueous phase. These microparticles appear in Table 6 below as "NaOleate-PLG (w/o/w)." Additionally, microparticles were prepared using NaOleate in an oil in water formulation, and these microparticles appear in Table 6 below as "NaOleate-PLG (o/w)." gp12 protein was adsorbed on the surface of the prepared microparticles as follows: 0.388 mg/ml of protein was added to about 20 mg of the microparticles in PBS to form a solution at about 1.4% w/w gp120/PLG in a total volume of 0.8 ml. The solutions were incubated for 1.5 hours at 37° C., then centrifuged. The supernatants were collected and then measured for protein content by microBCA. The results are shown in Table 6. The results confirm the superior adsorption of macromolecules by the microparticles of the present invention. T

TABLE 6

| Microparticle Type | protein | % bound (w/w gp120/PLG) | % total E2 bound |
|---|---|---|---|
| PVA-PLG | gp120 | 0.01 | 0.00 |
| PVA-PLG | gp120 | 0.09 | 3.00 |
| NaOleate-PLG (w/o/w) | gp120 | 1.33 | 96.00 |
| NaOleate-PLG (w/o/w) | gp120 | 1.24 | 95.00 |
| NaOleate-PLG (o/w) | gp120 | 0.41 | 31.00 |
| NaOleate-PLG (o/w) | gp120 | 0.27 | 20.00 |
| NaOleate-PLG (o/w) | gp120 | 0.36 | 28.00 |
| NaOleate-PLG (o/w) | gp120 | 0.27 | 22.00 |
| NaOleate-PLG (o/w) | gp120 | 0.34 | 26.00 |
| NaOleate-PLG (o/w) | gp120 | 0.31 | 24.00 |
| NaOleate-PLG (o/w) | gp120 | −0.01 | −1.00 |
| NaOleate-PLG (o/w) | gp120 | −0.09 | −7.00 |

EXAMPLE 10

Adsorption of Listeriolysin Protein

Microparticles were prepared using PVA and CTAB, as described in the previous examples. Listeriolysin protein (LLO) from Listeria monocytogenes was adsorbed on the surface of the microparticles as follows: 1.0 mg/ml LLO was added to 100 mg of the microparticles in PBS to form a solution at 1% w/w LLO/PLG in a total volume of 5 ml. The solutions were incubated for 1.5 hours at 37° C., then centrifuged. The supernatants were collected and then measured for protein content by microBCA. The results are shown in Table 7. The results confirm the superior adsorption of macromolecules by the microparticles of the present invention.

TABLE 7

| Microparticle Type | Protein | Targeted Load (% w/w) | Actual Load (% w/w) | Loading Efficiency |
|---|---|---|---|---|
| PVA-PLG | LLO | 0.10 | 0.10 | 10.0 |
| PVA-PLG | LLO | 0.25 | 0.08 | 32.0 |
| PVA-PLG | LLO | 0.50 | 0.12 | 24.0 |
| PVA-PLG | LLO | 1.00 | 0.18 | 18.0 |
| CTAB-PLG | LLO | 0.10 | 0.06 | 60.0 |
| CTAB-PLG | LLO | 0.25 | 0.19 | 76.0 |
| CTAB-PLG | LLO | 0.50 | 0.34 | 68.0 |
| CTAD-PLG | LLO | 1.00 | 0.71 | 71.0 |

EXAMPLE 11

Effect of Aluminum Salt as an Adjuvant p55 gag DNA-adsorbed PLG microparticles were prepared as described above, using CTAB. The microparticles were injected intramuscularly in mice at two concentrations, and, as a control, DNA alone was injected at the same two concentrations. Additionally, in one trial, 50 µg aluminum phosphate was added to the injected CTAB composition. Each formulation was injected into ten mice. The mice were boosted after 28 days. Two weeks after the second immunization, serum was collected and the geometric mean titer (GMT) of each serum was measured, along with its standard error (SE). The results are summarized in Table 8, presented as both linear and log values. Each number is the average of the results obtained from the ten mice.

TABLE 8

| Formulation | GMT | SE | log GMT | log SE |
|---|---|---|---|---|
| DNA-CTAB 1 µg | 19546 | 5983 | 4.28 | 0.11 |
| DNA-CTAB 10 µg | 54487 | 5510 | 4.73 | 0.04 |
| DNA-CTAB 1 µg + ALUM 50 µg | 49765 | 10034 | 4.69 | 0.1 |
| DNA alone 1 µg | 10.6 | 2.7 | 1.01 | 0.07 |
| DNA alone 10 µg | 230 | 395 | 2.15 | 0.3 |

In order to compare these results statistically, P-values were generated for DNA-CTAB vs. DNA-CTAB+ALUM (P-value=0.0017); DNA-CTAB+ALUM vs. DNA alone (P-value<0.0001); and DNA-CTAB (10 µg) vs. DNA alone (10 µg) (P-value<0.0001). These P-values confirm the statistical significance of the values in Table 8.

EXAMPLE 12

Measurement of Zeta Potentials

Measurement of zeta potentials was carried out on a DELSA 440 SX zetasizer from Coulter Corp., Miami, Fla. 33116. The system is calibrated using mobility standards from Coulter (EMP SL7, an aqueous suspension of polystyrene latex beads). Following rinsing of the sample cell with sterile water, samples are added to the sample cell. The counter is then set to zero by aligning the beam to its lowest value. The current is set at 0.7 mA for the reference and 20 V for the sample. Detector levels from all four beams are checked, then the sample is run by selecting "run" from the software, and frequency measurements are read. The beams should be 20 Hz apart. The mean zeta potential for each sample is then read.

Measurements for several microparticle formulations of the present invention were read, and the results are shown in Table 9. As the results indicate, absorbence of macromolecules to the microparticles' surfaces alters the zeta potentials of the microparticles.

TABLE 9

| Microparticle Type | Adherent macromolecule | Zeta Potential (mV) |
|---|---|---|
| PLG-PVA | none | −26 ± 8 |
| PLG-CTAB | none | +83 ± 22 |
| PLG-CTAB | p55 DNA | +35 ± 14 |
| PLG-SDS | none | −44 ± 26 |
| PLG-SDS | p55 protein | −32 ± 18 |
| PLG-Oleate | none | −64 ± 24 |
| PLG-Oleate | gp120 protein | −48 ± 14 |

EXAMPLE 13

Microparticles with Encapsulated and Adsorbed Macromolecules (A). PLG microparticles were prepared using RG 505 PLG and PVA, and encapsulating the adjuvant LTK63. 100 mg of the microparticles was incubated with 5 ml PBS containing 400 µg/ml p24gag protein. The mixture was then incubated with rocking at room temperature overnight, washed by centrifugation with 20 ml PBS twice and with water once, then lyophilized. Following base hydrolysis and neutralization, the % adsorbed protein and % encapsulated adjuvant were measured; the results appear in Table 10.

(B). PLG microparticles were prepared using SDS and RG 505 PLG, and encapsulating adjuvant CpG oligonucleotides as follows: 5 ml of 6% RG505 polymer in DCM was emulsified with 0.5 ml of 5 mg/ml CpG in 50 mM Tris/EDTA, forming a w/o emulsion. The w/o emulsion was added to 20 ml of 1% SDS and then emulsified, forming a w/o/w emulsion. Microparticles were formed by solvent evaporation overnight, then washed, centrifuged, and lyophilized. 10 mg of the CpG-encapsulated microparticles was dissolved in 1 ml DCM. 0.5 ml water was added to extract the oligonucleotides, and the mixture was then centrifuged and the aqueous layer was injected on a size exclusion column with PBS as the mobile phase. 10 mg of placebo microparticles was mixed with 100 µg CpG oligonucleotides and extracted as above with DCM and run on the column as a standard. The amount of CpG oligonucleotides present in the entrapped particles was calculated against the standard.

p55gag was adsorbed on the CpG-encapsulated microparticles as follows: 50 mg of the lyophilized CpG-encapsulated microparticles was incubated overnight with 5 ml 25 mM Borate with 6M Urea (pH 9) containing 140 µg p55gag protein. The mixture was incubated with rocking overnight at room temperature, washed with 20 ml Borate buffer/6M Urea twice, and 20 ml water twice, then lyophilized.

10 mg of the CpG-encapsulated/p55gag adsorbed microparticles was base hydrolyzed, and measurements were taken of the % entrapped and % adsorbed macromolecules. The targeted load was 1.0%, except as otherwise indicated. The results appear in Table 10.

TABLE 10

| Microparticle Type | % encapsulated (w/w) | % adsorbed (w/w) |
|---|---|---|
| (A). PLG-PVA LTK63 encapsulated p24gag adsorbed | 0.46 | 1.2* |
| (B). PLG-SDS CpG encapsulated p55gag adsorbed | 0.41 | 1.0 |

*targeted load = 2.0%

EXAMPLE 14

Microparticles with Two Adsorbed Macromolecules (A). According to the present invention, two or more macromolecules may be administered in a composition comprising microparticles which have adsorbed both macromolecules, or may be administered in a composition comprising two or more distinct microparticles, each having adsorbed a single macromolecule. For example, microparticles were prepared adsorbing both E2 polypeptide and adjuvant CpG oligonucleotides as follows: Blank PLG-CTAB were prepared as previously described. 20 mg of the lyophilized microparticles were incubated for 4 hours with 1 ml of 200 μg/ml E2 in saline. The mixture was rocked at room temperature for 4 hours, washed with 20 ml of normal saline water twice by centrifugation at 10,000 G, and the pellet was resuspended in 1 ml of a CpG solution in TE buffer containing 200 μg/ml CpG for 4 hours at room temperature. The final suspension was washed twice with TE buffer by centrifugation, and then lyophilized. 10 mg of the microparticles with adsorbed CpG and E2 was base hydrolyzed and protein concentration was determined by BCA, and the residual amount of CpG in the supernatant was assayed by HPLC to measure the amount of CpG adsorbed on the microparticles. The results appear in Table 11, demonstrating positive adsorption for both macromolecules.

(B). Microparticles were prepared according to the invention. A portion were used to adsorb E2 polypeptide, while another portion was used to adsorb adjuvant CpG olignucleotides. Blank PLG-CTAB were prepared as previously described. 20 mg of the lyophilized microparticles were incubated for 4 hours with 1 ml of 200 μg/ml E2 in saline. The mixture was rocked at room temperature for 4 hours, washed with 20 ml of normal saline water twice by centrifugation at 10,000 G, then lyophilized. Separately, 20 mg of the lyophilized microparticles were incubated for 4 hours with 1 ml of 200 μg/ml CpG in TE buffer. The mixture was rocked at room temperature for 4 hours, washed with 20 ml of TE buffer twice by centrifugation at 10,000 G, then lyophilized. Results of measurements of the percent adsorbed macromolecules appears in Table 11.

TABLE 11

| Microparticle Type | % adsorbed E2 (w/w)* | % adsorbed CpG (w/w)* |
|---|---|---|
| (A). PLG-SDS E2 adsorbed CpG adsorbed | 0.71 | 0.32 |
| (B). PLG-SDS E2 adsorbed | 0.64 | n/a |
| (B). PLG-SDS CpG adsorbed | n/a | 0.81 |

*targeted load = 1.0%

EXAMPLE 15

Microparticles Formed Using Combination of Detergent and PVA

The following procedure was used to form microparticles comprising two surfactants: PVA and a detergent: 10 ml of 5% PLG polymer and 0.2% of the detergent DOTAP in DCM were emulsified at 12,000 rpm for 3 minutes with 1.0 ml distilled water to form the primary w/o emulsion. The w/o emulsion was added to 40 ml of 0.8% PVA and emulsified for 3 minutes to form the second w/o/w emulsion, which was stirred overnight to evaporate the solvent, and microparticles were formed. The microparticles were washed twice in distilled water and lyophilized. The microparticles are then ready for adsorption of macromolecules in accordance with the present invention.

The same procedure was employed to form microparticles comprising a combination of PVA and the detergent DDA.

EXAMPLE 16

Immunogenicity of Microparticles With Adsorbed p55 DNA

Microparticles were formed as in the previous examples using the detergents CTAB or DDA. p55 DNA was adsorbed to the microparticles and immunogenicity was assessed using the procedures described in in the previous examples. The results are summarized in Table 12 below.

TABLE 12

PERCENT SPECIFIC LYSIS OF TARGETS

| Effector | E:T Ratio | Sv/B P7g[a] |
|---|---|---|
| PLG-CTAB/p55 DNA | 60:1 | 71 |
| 1 μg | 15:1 | 55 |
| | 4:1 | 31 |

TABLE 12-continued

PERCENT SPECIFIC LYSIS OF TARGETS

| Effector | E:T Ratio | Sv/B P7g[a] |
|---|---|---|
| PLG-DDA/p55 | 60:1 | 70 |
| 1 μg | 15:1 | 54 |
|  | 4:1 | 17 |
| p55 DNA alone | 60:1 | 3 |
| 1 μg | 15:1 | 1 |
|  | 4:1 | 0 |
| Vaccinia gag | 60:1 | 64 |
| 2 × 10[7] pfu | 15:1 | 35 |
|  | 4:1 | 11 |

[a]SVB cell line pulsed with gag b peptide

EXAMPLE 17

In-Vivo Luciferase Expression Using Microparticles With Adsorbed Luciferase DNA

Microparticles were formed using the above-described procedures using PLG and the detergent CTAB. Luciferase DNA was adsorbed thereon using the methods previously described. In vitro luciferase expression using a 5 μg dose of luciferase DNA was measured using the luciferase DNA alone (1248 pg) and the microparticles with luciferase DNA adsorbed thereon (2250 pg). In vivo luciferase expression was measured in muscle on days 1 and 14 following administration as follows: Two groups of mice (n=5) were each injected with either 50 μg of Luciferase plasmid or 50 μg of PLG-CTAB-Luciferase DNA microparticles. Both groups of mice were injected intramuscularly in the anterior tibialis (TA) muscle on two legs. Both TA muscles from each mouse in the two groups were harvested either at day 1 or day 14 and stored in a −80C. freezer. The muscles were ground with a mortar and pestle on dry ice. The powdered muscles were collected in eppendorf tubes with 0.5 ml of 1×Reporter Lysis Buffer.

The samples were vortexed for 15 minutes at room temperature. After freeze/thawing 3x, the samples were spun at 14,000 rpm for 10 minutes. The supernatant of the TA muscles of each mice at each timepoint were pooled and 20 ul of the samples were assayed using an ML3000 (Dynatech) under enhanced flash for Luciferase expression.

Luciferase determination was performed using a chemiluminiscence assay. The buffer was prepared containing 1 mg/ml of BSA in 1× Reporter Lysis (Promega). The luciferase enzyme stock (Promega) at 10 mg/ml was used as a standard, diluted to a concentration of 500 pg/20 ul. This standard was serially diluted 1:2 down the Microlite 2 plate (Dynatech) to create a standard curve. 20 μl of the blank and the samples were also placed on the plate and were serially diluted 1:2. The plates were placed in the ML3000 where 100 ul of the Luciferase Assay Reagent (Promega) were injected per well. Under enhanced flash, the relative light units were measured for each sample.

The results are tabulated below in Table 13.

TABLE 13

| Microparticle Type | In vivo luciferase expression Day 1 (pg) | In vivo luciferase expression Day 14 (pg) |
|---|---|---|
| PLG-CTAB Luciferase DNA adsorbed (50 ug) | 9.51 | 44.95 |

TABLE 13-continued

| Microparticle Type | In vivo luciferase expression Day 1 (pg) | In vivo luciferase expression Day 14 (pg) |
|---|---|---|
| Luciferase DNA alone (50 ug) | 6.78 | 9.29 |

EXAMPLE 18

Immunogenicity of Microparticles with Adsorbed vs. Entrapped Antigen

Microparticles were prepared using the procedures discussed in the previous examples. E2 protein was then adsorbed thereon as described above. Microparticles were also prepared with E2 entrapped therein, rather than adsorbed thereon, as described above. The microparticles were assessed for their ability to induce IgG antibodies following immunization of 10 mice with each type of microparticle. The geometric mean titer (GMT) of serum from each mouse was measured, then averaged for the group of 10 animals. Standard error (SE) was also calculated. Fisher's PLSD (significance level 5% ) was measured at p=0.0006. The results are shown in Table 14 below: The results clearly demonstrate superior induction of humoral immune response using the adsorbed microparticles of the present invention.

TABLE 14

| Formulation | GMT | SE |
|---|---|---|
| PLG with entrapped E2 | 293 | 270 |
| PLG with adsorbed E2 | 3122 | 1310 |

EXAMPLE 19

Immunogenicity of Microparticles with HCV E1E2 Protein Adsorbed Thereon

PLG-CTAB microparticles were prepared using the procedures discussed in the previous examples. E1E2 protein from Hepatitis C Virus (HCV) was adsorbed thereon. The particles were used to immunize mice, with or without the adjuvant Alum, in dosages of microparticles calculated to provide either 10 μg or 100 μg of protein. Geometric mean titer was measured, and the results are shown below in Table 15.

TABLE 15

| Formulation | GMT | SE |
|---|---|---|
| PLG/CTAB E1E2 (10 μg) | 4117 | 558 |
| PLG/CTAB E1E2 (100 μg) | 7583 | 659 |
| PLG/CTAB E1E2 Alum (10 μg) | 3356 | 436 |
| PLG/CTAB E1E2 Alum (100 μg) | 10485 | 1548 |
| HCV E1E2 DNA (10 μg) | 87 | 63 |
| HCV E1E2 DNA (100 μg) | 7621 | 571 |

As the results indicate, the microparticles with protein adsorbed thereon produce a superior immune response at the 10 μg dose. This demonstrates that the microparticles have the advantage of being useful in eliciting immune responses at low doses where free DNA is unable to generate such responses.

EXAMPLE 20

Immunogenicity of Microparticles with Adsorbed p24 Gag Protein

PLG-PVA microparticles were prepared using the procedures discussed in the previous examples. The protein p24 gag was then adsorbed thereon as described above. The microparticles were assessed for their ability to induce IgG, IgG1, and IgG2a antibodies following immunizations of of 10 mice. The geometric mean titer (GMT) of serum collected from the mice 2 weeks post $2^{nd}$ immunization (2wp2) and 2 weeks post $3^{rd}$ immunization (2wp3) were measured, then averaged for the group of 10 animals. Standard error (SE) was also calculated. The results are shown in Table 16 below: The results clearly demonstrate superior induction of humoral immune response using the adsorbed microparticles of the present invention.

TABLE 16

|  | IgG GMT | IgG SE | IgG1 GMT | IgG1 SE | IgG2a GMT | IgG2a SE |
|---|---|---|---|---|---|---|
| PLG-PVA/p24 gag (2wp2) | 5813.59 | 2400.58 | 3741.17 | 2039.08 | 755.3 | 587.21 |
| p24 gag alone (2wp2) | 6.6 | 7.91 | 6.51 | 6.85 | 5 | 1 |
| PLG-PVA/p24 gag (2wp3) | 26730.29 | 3443.67 | 40088.65 | 8989.07 | 6974.22 | 1457.74 |
| p24 gag alone (2wp3) | 7.15 | 5.59 | 8.22 | 12.3 | 5 | 1 |

EXAMPLE 21

IM Immunization of p55 Gag Protein and Various Adjuvants

PLG/CTAB, PLG/SDS, and PLG/PVA microparticles were formed as described above in the previous examples. Eight groups of microparticles were made in order to analyze the different effects of immunizing mice with adsorbed antigen p55 gag protein on microparticles vs. providing free soluble p55 gag, and to determine the effects of having the adjuvant CpG (20 base long single stranded oligonucleotides with a CpG motif) also adsorbed on other microparticles or provided in free soluble form. The different groups were prepared as follows:

Group 1 used soluble p55 gag protein (recombinant HIV p55 gag protein produced in yeast at 2 mg/ml in tris/NaCl buffer with 2M urea) mixed with PLG/CTAB particles with adsorbed CpG.

Group 2 used PLG/SDS particles with adsorbed p55 gag mixed with PLG/CTAB particles with adsorbed CpG.

Group 3 used PLG/SDS particles with adsorbed p55 gag mixed with free CpG.

Group 4 used PLG/SDS particles with adsorbed p55 gag and no adjuvant.

Group 5 used PLG/PVA particles with p55 gag entrapped therein mixed with PLG/CTAB particles with CpG adsorbed.

Group 6, a control, used no antigen, and soluble CpG.

Group 7, another control, used soluble p55 gag protein and no adjuvants. Group 8, another control, used only vaccinia virus (vv gag) expressing the gag gene, and no adjuvants.

For each group, 10 mice were immunized with sufficient quantities of microparticles or free molecules such that the dosage of p55 gag antigen and CpG adjuvant were 25 μg each (if present in the group), except for Group 8 which was used at a dosage of $10 \times 10^7$ pfu. The route of immunization was IM, except for Group 8, which route was IP. Following immunization, serum anti-p55 IgG titer was measured, the results of which appear below in Table 17. Lysis of targets by CTL was also measured with each group, the results of which appear below in Table 18.

TABLE 17

Serum IgG Titer

| Group | Form of p55 gag Protein Antigen | Form of CpG Adjuvant | Serum Titer |
|---|---|---|---|
| 1 | soluble | adsorbed on PLG/CTAB particles | 43250 |
| 2 | adsorbed on PLG/SDS particles | adsorbed on PLG/CTAB particles | 49750 |
| 3 | adsorbed on PLG/SDS particles | soluble | 62750 |
| 4 | adsorbed on PLG/SDS particles | none | 7550 |
| 5 | entrapped within PLG/PVA particles | adsorbed on PLG/CTAB particles | 127000 |
| 6 | soluble | soluble | 38 |
| 7 | soluble | none | 2913 |
| 8 | vaccinia virus (vv gag) | none | 938 |

TABLE 18

PERCENT SPECIFIC LYSIS OF TARGETS

| Group | Form of p55 gag Protein Antigen | Form of CpG Adjuvant | Target Ratio | SvB pGAG[a] | SvB P7g+[b] |
|---|---|---|---|---|---|
| 1 | soluble | adsorbed on PLG/CTAB particles | 60 | 3 | 41 |
|  |  |  | 15 | 0 | 15 |
|  |  |  | 4 | -1 | 8 |
| 2 | adsorbed on PLG/SDS particles | adsorbed on PLG/CTAB particles | 60 | 7 | 77 |
|  |  |  | 15 | 4 | 49 |
|  |  |  | 4 | 2 | 26 |
| 3 | adsorbed on PLG/SDS particles | soluble | 60 | 6 | 51 |
|  |  |  | 15 | 3 | 30 |
|  |  |  | 4 | 4 | 11 |
| 4 | adsorbed on PLG/SDS particles | none | 60 | 4 | 48 |
|  |  |  | 15 | 2 | 21 |
|  |  |  | 4 | 1 | 7 |
| 5 | entrapped within PLG/PVA particles | adsorbed on PLG/CTAB particles | 60 | 3 | 37 |
|  |  |  | 15 | 2 | 17 |
|  |  |  | 4 | 0 | 4 |
| 6 | soluble | soluble | 60 | 4 | 23 |
|  |  |  | 15 | 4 | 7 |
|  |  |  | 4 | 2 | 3 |
| 7 | soluble | none | 60 | 1 | 4 |
|  |  |  | 15 | -1 | 1 |
|  |  |  | 4 | 0 | 2 |
| 8 | vaccinia virus (vv gag) | none | 60 | 3 | 52 |
|  |  |  | 15 | 2 | 25 |
|  |  |  | 4 | 3 | 16 |

[a]SvB cell line pulsed with irrelevant peptide
[b]SvB cell line pulsed with p7g peptide

EXAMPLE 22

Adsorption vs. Entrapment of p55 DNA

PLG/CTAB microparticles with adsorbed p55 DNA, and PLG/PVA microparticles with p55 DNA entrapped within, were formed as described above in the previous examples. IM immunization of mice and antibody induction (collection and analysis of serum) were performed as described in the previous examples, at four weeks post 1$^{st}$ immunization (4wp1), and 2, 4, 6, 13, and 15 weeks post 2$^{nd}$ immunization (2wp2, 4wp2, 6wp2, 13wp2, and 15wp2 respectively). The results, shown in Table 19 below, demonstrate a clear advantage of the adsorbed microparticles over both entrapped and free p55.

TABLE 19

| Formulation | 4wp1 | 2wp2 | 4wp2 | 6wp2 | 13wp2 | 15wp2 |
|---|---|---|---|---|---|---|
| PLG/CTAB with p55 DNA adsorbed (1 μg) | 576 | 79300 | 156000 | 227000 | 988000 | 123000 |
| PLG/PVA with p55 DNA entrapped (1 μg) | 996 | 1915 | 2215 | 1376 | 25100 | 1084 |
| p55 plasmid alone (1 μg) | 912 | 1149 | 1360 | 701 | 1075 | 742 |
| p55 plasmid alone (10 μg) | 1489 | 10700 | 7885 | 26300 | 31600 | 17300 |

EXAMPLE 23

Microparticle Induction of Immune Response in Guinea Pigs

PLG/CTAB microparticles with adsorbed gp120DNA were formed as described above in the previous examples. Other samples are as shown below in Table 20, and included the microparticles with and without aluminium phosphate, controls of free soluble gp120, with and without aluminium phosphate, and MF59 protein, encoded by gp120 DNA. IM immunization of guinea pigs and antibody induction (collection and analysis of serum) were performed as described in the previous examples. The results are shown in Table 20 below.

TABLE 20

| Formulation | GMT | SE |
|---|---|---|
| PLG/CTAB gp120 adsorbed (25 μg) | 1435 | 383 |
| PLG/CTAB gp120 adsorbed (25 μg) + Alum. phosphate | 3624 | 454 |
| soluble gp120 DNA (25 μg) + Alum phosphate | 119 | 606 |
| soluble gp120 DNA (25 μg) alone | 101 | 55 |
| MF59 protein (50 μg) | 3468 | 911 |

EXAMPLE 24

Intranasal (IN) Immunization with p55 DNA Adsorbed Microparticles

PLG/CTAB microparticles with adsorbed p55 DNA, and PLG/DDA microparticles with adsorbed p55 DNA, were formed as described above in the previous examples. IN immunization of mice with 25 or 100 μg, antibody induction (collection and analysis of serum), and CTL induction were performed as described in the previous examples, at two and four weeks post 1$^{st}$ immunization (2wp1, 4wp1), two and four weeks post 2$^{nd}$ immunization (2wp2, 4wp2), and two and four weeks post 3$^{rd}$ immunization (2wp3, 4wp3). Controls included immunization with soluble p55 DNA alone or with 10 μg cholera toxin. The results for antibody induction are shown in Table 21, and the results for lysis by CTL (at 4 weeks post 4$^{th}$ immunization) are shown in Table 22 below.

TABLE 21

| Formulation | 2wp1 | 4wp2 | 2wp2 | 4wp2 | 2wp3 | 4wp3 |
|---|---|---|---|---|---|---|
| PLG/CTAB with p55 DNA adsorbed (25 μg) | 189 | 529 | 1412 | 882 | 908 | 742 |
| PLG/CTAB with p55 DNA adsorbed (100 μg) | 128 | 383 | 3462 | 2887 | 289000 | 134000 |
| PLG/DDA with p55 DNA adsorbed (25 μg) | 247 | 482 | 1223 | 338 | 940 | 545 |
| PLG/DDA with p55 DNA adsorbed (100 μg) | 143 | 1351 | 2538 | 1341 | 357000 | 161000 |
| soluble p55 DNA (100 μg) + cholera toxin (10 μg) | 195 | 270 | 2298 | 617 | 1549 | 862 |
| soluble p55 DNA (100 μg) alone | 362 | 260 | 618 | 190 | 285 | 263 |

TABLE 22

PERCENT SPECIFIC LYSIS OF TARGETS

| Group | Formulation | Dose of p55 DNA | Target Ratio | SvB pGAG[a] | SvB P7g+[b] |
|---|---|---|---|---|---|
| 1 | PLG/CTAB with adsorbed p55 DNA | 100 μg | 60 | −1 | 82 |
|  |  |  | 15 | −1 | 53 |
|  |  |  | 4 | 12 | 25 |
| 2 | PLG/DDA with adsorbed p55 DNA | 100 μg | 60 | 10 | 47 |
|  |  |  | 15 | 3 | 26 |
|  |  |  | 4 | 2 | 8 |
| 3 | p55 DNA plus cholera toxin (10 μg) | 100 μg | 60 | 9 | 64 |
|  |  |  | 15 | 2 | 22 |
|  |  |  | 4 | 0 | 7 |
| 4 | p55 DNA alone | 100 μg | 60 | 4 | 6 |
|  |  |  | 15 | 2 | 3 |
|  |  |  | 4 | 1 | 1 |

[a]SvB cell line pulsed with irrelevant peptide
[b]SvB cell line pulsed with p7g peptide Although preferred embodiments of the subject invention have been described in some detail, it is understood that obvious variations can be made without departing from the spirit and the scope of the invention as defined by the appended claims.

We claim:

1. A microparticle comprising: a polymer selected from the group consisting of a poly(α-hydroxy acid), a polyhydroxy butyric acid, a polycaprolactone, a polyorthoester, a polyanhydride, and a polycyanoacrylate; a cationic detergent; and an antigen comprising a polynucleotide adsorbed on the surface of said microparticle,
   wherein said microparticle is formed by a process that comprises: forming a microparticle comprising said polymer and said detergent, said microparticle being formed in the presence of said detergent; and exposing said microparticle to said antigen.

2. The microparticle of claim 1, further comprising an additional biologically active macromolecule encapsulated within said microparticle, wherein the additional biologically active macromolecule is selected from a polypeptide, a polynucleotide, a polynucleoside, an antigen, a hormone, an enzyme, and an immunological adjuvant.

3. The microparticle of claim 2, wherein the additional biologically active macromolecule is an immunological adjuvant.

4. The microparticle of claim 3, wherein the immunological adjuvant is an aluminum salt.

5. The microparticle of claim 1, wherein the poly(α-hydroxy acid) is selected from poly(L-lactide), poly(D,L-lactide) and poly(D,L-lactide-co-glycolide).

6. The microparticle of claim 1, wherein the polymer is poly(D,L-lactide-co-glycolide).

7. The microparticle of claim 1, wherein said polynucleotide encodes a polypeptide selected from an HIV gp 160polypeptide, an HIV p24gag polypeptide, an HIV p55gag polypeptide, and an Influenza A hemagglutinin polypeptide.

8. The microparticle of claim 1, wherein said polynucleotide encodes an HIV gp 120 polypeptide.

9. The microparticle of claim 1 wherein the cationic detergent is hexadecyltrimethylammonium bromide.

10. A microparticle composition comprising a microparticle of any one of claims 1, 2–6 and 7–4 and a pharmaceutically acceptable excipient.

11. The microparticle composition of claim 10, wherein said microparticle composition is an injectable composition.

12. A microparticle composition comprising a microparticle according to any one of claims 1, 5, 6, 7 and 8, a pharmaceutically acceptable excipient, and an immunological adjuvant.

13. A microparticle composition of claim 12, wherein the immunological adjuvant is selected from CpG oligonucleotides, *E. coli* heat-labile toxin-K63 (LTK63), *E. coli* heat-labile toxin-R72 (LTR72) monophosphorylipid A (MPL), and an aluminum salt.

14. A microparticle composition of claim 13, wherein the aluminum salt is aluminum phosphate.

15. The microparticle composition of claim 12, wherein said microparticle composition is an injectable composition.

16. The microparticle of any one of claims 1, 2–6 and 7–4, wherein said polynucleotide is a plasmid DNA molecule.

17. A microparticle composition comprising a microparticle of claim 16 and a pharmaceutically acceptable excipient.

18. The microparticle composition of claim 17, wherein said microparticle composition is an injectable composition.

19. The microparticle of any of claims 1, 2–6, 3 and 4, wherein the polynucleotide encodes a polypeptide selected from HIV polypeptides, hepatitis B virus polypeptides, hepatitis C virus polypeptides, *Haemophilus influenza* type B polypeptides, pertussis polypeptides, diphtheria polypeptides, tetanus polypeptides, and influenza A virus polypeptides.

20. A microparticle composition comprising a microparticle of claim 19 and a pharmaceutically acceptable excipient.

21. The microparticle composition of claim 20, wherein said microparticle composition is an injectable composition.

22. The microparticle of any one of claims 1, 2–6, 7–4 and 9, wherein said microparticle does not comprise an entrapped antigen.

23. The microparticle of any one of claims 1, 2–6, 7–4 and 9, wherein said microparticle is formed in a double emulsion process.

24. The microparticle of any one of claims 1, 2–6, 3, 4 and 9, wherein the polynucleotide encodes a polypeptide derived from a pathogenic organism.

25. The microparticle of claim 24 wherein said pathogenic organism is a bacterium.

26. The microparticle of claim 24, wherein said pathogenic organism is a virus.

27. A microparticle composition comprising a microparticle of claim 24 and a pharmaceutically acceptable excipient.

28. The microparticle composition of claim 27, wherein said microparticle composition is an injectable composition.

29. The microparticle of any one of claims 1, 2–6, 7–4 and 9, wherein the microparticle has a diameter between 500 nanometers and 10 microns.

30. A microparticle composition comprising a microparticle of claim 29 and a pharmaceutically acceptable excipient.

31. The microparticle composition of claim 30, wherein said microparticle composition is an injectable composition.

32. The microparticle of any one of claims 1, 2, 5, 6, 3 and 4, wherein said polynucleotide encodes a polypeptide derived from a tumor antigen.

33. A microparticle composition comprising a microparticle of claim 32 and a pharmaceutically acceptable excipient.

34. The microparticle composition of claim 32 wherein said microparticle composition is an injectable composition.

35. The microparticle of any one of claims 2, 7–4 and 9, wherein the polymer is poly(D,L-lactide-co-glycolide).

36. A microparticle composition comprising a microparticle of claim 35 and a pharmaceutically acceptable excipient.

37. The microparticle composition of claim 36, wherein said microparticle composition is an injectable composition.

38. A method of raising an immune response, comprising:
providing the microparticle composition of claim 10, and administering said microparticle composition to a vertebrate animal.

39. A method of raising an immune response, comprising:
providing the microparticle composition of claim 12, and administering said microparticle composition to a vertebrate animal.

40. A method of raising an immune response, comprising:
providing the microparticle composition of claim 17, and administering said microparticle composition to a vertebrate animal.

41. A method of raising an immune response, comprising:
providing the microparticle composition of claim 30, and administering said microparticle composition to a vertebrate animal.

42. A method of raising an immune response, comprising:
providing the microparticle composition of claim 36, and administering said microparticle composition to a vertebrate animal.

43. A method of raising an immune response, comprising:
providing the microparticle composition of claim 20, and administering said microparticle composition to a vertebrate animal.

44. A method of raising an immune response, comprising:
providing the microparticle composition of claim 27, and administering said microparticle composition to a vertebrate animal.

45. A method of raising an immune response, comprising:
providing the microparticle composition of claim 33, and administering said microparticle composition to a vertebrate animal.

46. A microparticle comprising: a biodegradable polymer; a cationic detergent; and an antigen comprising a polynucleotide adsorbed on the surface of said microparticle, wherein said microparticle is formed by a process that comprises: forming a microparticle comprising said polymer and said detergent, said microparticle being formed in the presence of said detergent; and exposing said microparticle to said antigen.

47. The microparticle of claim 46, further comprising an additional biologically active macromolecule encapsulated within said microparticle, wherein the additional biologically active macromolecule is selected from a polypeptide, a polynucleotide, a polynucleoside, an antigen, a hormone, an enzyme, and an immunological adjuvant.

48. A microparticle composition comprising a microparticle of any one of claims 46 and 47 and a pharmaceutically acceptable excipient.

49. The microparticle composition of claim 48, wherein said microparticle composition is an injectable composition.

50. A microparticle composition comprising a microparticle according to any one of claims 46 and 47 a pharmaceutically acceptable excipient, and an immunological adjuvant.

51. The microparticle of composition of claim 50, wherein said microparticle composition is an injectable composition.

52. A method of raising an immune response, comprising:
providing the microparticle composition of claim 48, and administering said microparticle composition to a vertebrate animal.

53. A method of raising an immune response, comprising:
providing the microparticle composition of claim 50, and administering said microparticle composition to a vertebrate animal.

* * * * *

UNITED STATES PATENT AND TRADEMARK OFFICE
CERTIFICATE OF CORRECTION

PATENT NO. : 6,884,435 B1
DATED : April 26, 2005
INVENTOR(S) : Derek O'Hagan, Manmohan Singh and Gary Ott It is certified that error appears in the above-identified patent and that said Letters Patent is hereby corrected as shown below:

Column 31,
Lines 21 and 38, delete "1, 2-6 and 7-4" and insert in lieu thereof -- 1-8 --;
Line 45, delete "1, 2-6, 3 and 4" and insert in lieu thereof -- 1-6 --;
Lines 57 and 60, delete "1, 2-6, 7-4 and 9" and insert in lieu thereof -- 1-9 --;
Line 63, delete "1, 2-6, 3, 4 and 9" and insert in lieu thereof -- 1-6 and 9 --;

Column 32,
Line 8, delete "1, 2-6, 7-4 and 9" and insert in lieu thereof -- 1-9 --;
Line 21, delete "32" and insert in lieu thereof -- 33 --; and
Line 23, delete "2, 7-4 and 9" and insert in lieu thereof -- 2-4 and 7-9 --.

Signed and Sealed this

Twenty-third Day of August, 2005

JON W. DUDAS
*Director of the United States Patent and Trademark Office*